US00PP16038P3

(12) United States Plant Patent
Jensen

(10) Patent No.: US PP16,038 P3
(45) Date of Patent: Oct. 18, 2005

(54) ***CAMPANULA* PLANT NAMED 'PKMH02'**

(50) Latin Name: *Campanula×haylodgensis hort*
Varietal Denomination: PKMh02

(75) Inventor: Gert Kim Jensen, Sohus (DK)

(73) Assignee: Gartneriet PKM ApS (DK)

( * ) Notice: Subject to any disclaimer, the term of this patent is extended or adjusted under 35 U.S.C. 154(b) by 0 days.

(21) Appl. No.: 10/717,654

(22) Filed: Nov. 21, 2003

(65) Prior Publication Data

US 2005/0114961 P1 May 26, 2005

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct cultivar of *Campanula* plant named 'PKMh02', characterized by having compact plant habit; freely branching plant form; vigorous growth habit and less need for chemical growth retardation; greater number of larger flowers per plant, and large upright pale blue flowers.

5 Drawing Sheets

Latin name of genus and species of the plant claimed: *Campanula×haylodgensis hort.*
Variety denomination: PKMh02.

BACKGROUND OF THE INVENTION

The present invention relates to a new and distinct cultivar of *Campanula* plant, botanically known as *Campanula× haylodgensis hort.,* commonly known as Bellflower, and hereinafter referred to by the name 'PKMh02'.

The new *Campanula*, 'PKMh02', is a product of a planned breeding program conducted by the Inventor, Gert K. Jensen, in Søhus, Denmark. The new *Campanula* originated as a mutant in a production batch of an unnamed, proprietary selection of *Campanula×haylodgensis hort.* (unpatented). The Inventor selected the new *Campanula* cultivar from the progeny of the above cross on the basis of its compact and freely flowering habit with upright, pale blue flowers. Plants of the new *Campanula* are more upright, compact, and more freely flowering with larger flowers than the original cultivar.

Asexual reproduction of the new cultivar by terminal cuttings taken and propagated in Søhus, Denmark, has shown that the unique features of this new *Campanula* are stable and reproduce true to type in many successive generations.

SUMMARY OF THE INVENTION

Plants of the cultivar 'PKMh02' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'PKMh02'. These characteristics in combination distinguish 'PKMh02' as a new and distinct cultivar:

1. Upright plant habit;
2. Greater number of larger flowers per plant;

3. Vigorous growth habit, and less need for chemical growth retardation;
4. Upright, pale blue double flowers; and
5. Balloon shaped flower buds.

Side-by-side comparisons between the instant plant and an unnamed proprietary selection of *Campanula× haylodgensis hort.* were conducted by the Inventor in Søhus, Denmark. Plants of 'PKMh02' differ from the unnamed proprietary selection of *Campanula×haylodgensis hort.* in the following characteristics:

1. Plants of 'PKMh02' have more lateral branches and more upright growth than plants of the unnamed proprietary selection of *Campanula×haylodgensis hort.*
2. Plants of 'PKMh02' have differently shaped leaves than plants of similar cultivars of the unnamed proprietary selection of *Campanula×haylodgensis hort.*
3. Plants of 'PKMh02' have longer peduncles than plants of the unnamed proprietary selection of *Campanula× haylodgensis hort.*
4. Plants of 'PKMh02' have lighter blue colored flowers than plants of the unnamed proprietary selection of *Campanula×haylodgensis hort.*
5. Plants of 'PKMh02' have more flowers per plant and larger flowers than plants of the unnamed proprietary selection of *Campanula×haylodgensis hort.*
6. Plants of 'PKMh02' have more upright flowers than plants of the unnamed proprietary selection of *Campanula×haylodgensis hort.*

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'PKMh02'.

The first photographic drawing shows a flower of 'PKMh02', designated in the photograph by the breeder's reference. 'Elizabeth Wonder', as compared to a flower of an unnamed proprietary selection of *Campanula×haylodgensis hort.*

The second photographic drawing shows a close-up view of typical flowering racemes of 'PKMh02', designated in the photograph by the breeder's reference, 'Elizabeth Wonder', as compared to typical flowering racemes of an unnamed proprietary selection of *Campanula×haylodgensis hort.*

The third photographic drawing shows a side view of a potted flowering plant of 'PKMh02'.

The fourth photographic drawing shows a view of typical flowers and leaves produced by 'PKMh02'.

The fifth photographic drawing shows a top perspective view of a typical flowering plant of 'PKMh02' compared to the 'Blue Wonder' named proprietary selection of *Campanula×haylodgensis hort.* as grown in 11 cm pots.

DETAILED BOTANICAL DESCRIPTION

In the following description, color references are made to The Royal Horticultural Society (R.H.S.) Colour Chart, $4^{th}$ edition, where general terms of ordinary dictionary significance are used. Plants were grown under greenhouse conditions. The plants described were about 14 weeks old after cutting, as grown in 11 cm pots.

Parentage: Mutant of unnamed proprietary selection of *Campanula×haylodgensis hort* (unpatented).

Propagation:

*Type cutting.*—Terminal vegetative cuttings.

*Time to initiate roots.*—About 10 to 14 days at 18 to 21 C in tunnels in a greenhouse.

*Root description.*—Fine, well branched.

Plant description:

*Form.*—Perennial plant with upright plant habit. Double, campanulate flowers in racemes. Freely branching with lateral branches forming at every node, dense and bushy.

*Crop time.*—After rooting, about 13 weeks are required to produce finished flowering plants in 11 cm pots.

*Plant height* (*soil level to top of plant plane*).—About 20 cm.

*Vigor.*—Vigorous growth rate.

Foliage description: Basal leaves single, dentate, cordate, palmate venation.

*Length.*—20–30 mm.

*Width.*—About 25 mm.

*Shape.*—Cordate.

*Apex.*—Truncate.

*Base.*—Cuspidate.

*Margin.*—Broadly crenate.

*Texture.*—Smooth, glabrous, dull. No pubescence.

*Upper leaves* (*bracts*).—Single, entire, Oblong. Tips acute, bases cuneate.

*Length.*—25–30 mm.

*Width.*—20 mm.

*Color.*—Young foliage, upper and lower surfaces: from RHS 138A to RHS 138 C, green.

*Mature foliage, upper and lower surfaces.*—RHS 143 A and RHS 138 B, respectively.

Flower description:

*Flower arrangement and shape.*—Double, hose in hose flowers in racemes; campanulate flowers with small star shaped calyx. The calyx is medium green, RHS 138A.

*Natural flowering season.*—Continuous throughout the spring and summer. Season can be extended by vernalization and long day treatments.

*Flower longevity on the plant.*—Longevity of individual flowers is highly dependent on temperature and light conditions. Flowers persistent.

*Inflorescence size.*—Length: about 14 cm.

*Number of flowers per inflorescence.*—8; about 500 flowers per plant.

*Flower buds.*—Upright balloon shape.

*Flowers.*—Upright. Depth: About 12 mm. Diameter: About 25 mm. Lanceolate, acuminate petal lobes: 5 mm long and 8 mm wide. Young corolla color: upper and lower surfaces, RHS 91 D and RHS 91 C, respectively, pale blue violet; older petals upper and lower are RHS 97 D and RHS 85 C, respectively.

Peduncle:

*Strength.*—Moderately weak.

*Length.*—About 7–20 mm.

*Diameter.*—About 0.2 mm.

*Color.*—RHS 138 A, light green.

Reproductive organs: Pistil and stigma are contorted, same color as petals.

Weather tolerance: Plants of the new *Campanula* have exhibited good tolerance to drought, rain and wind; low temperature resistant to −20C.

I claim:

1. A new and distinct cultivar of *Campanula* plant named 'PKMh02', as illustrated and described herein.

* * * * *

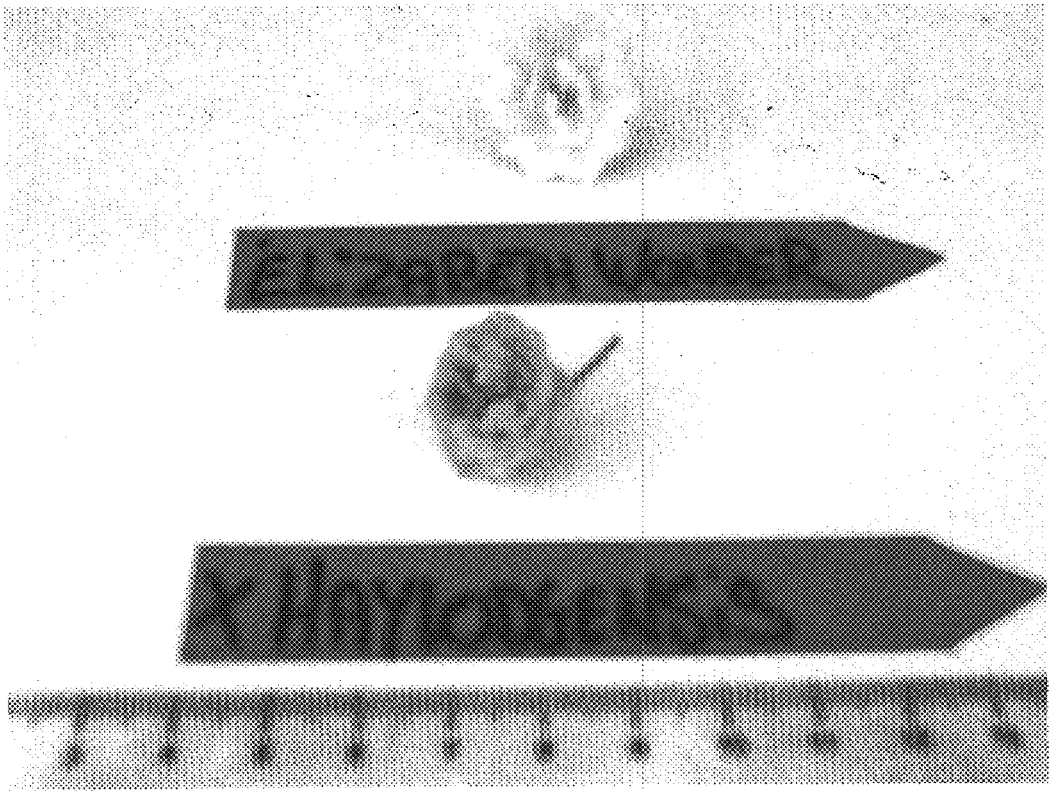
Elizabeth Walker
Xylopyrus

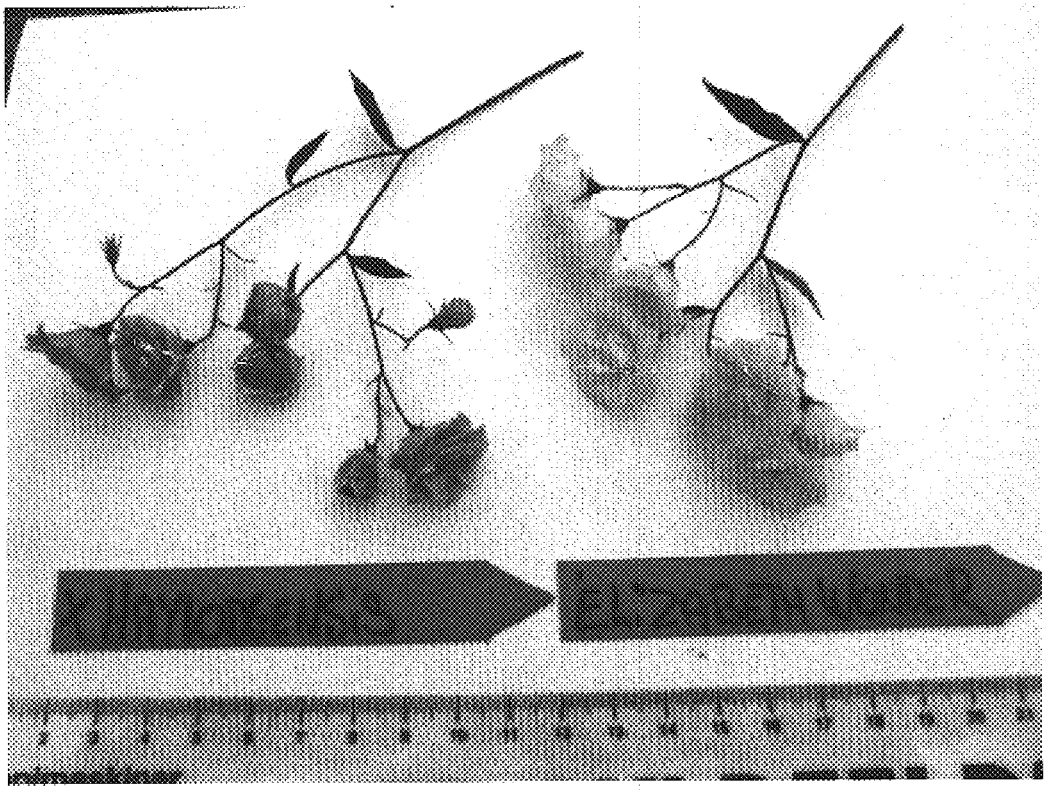

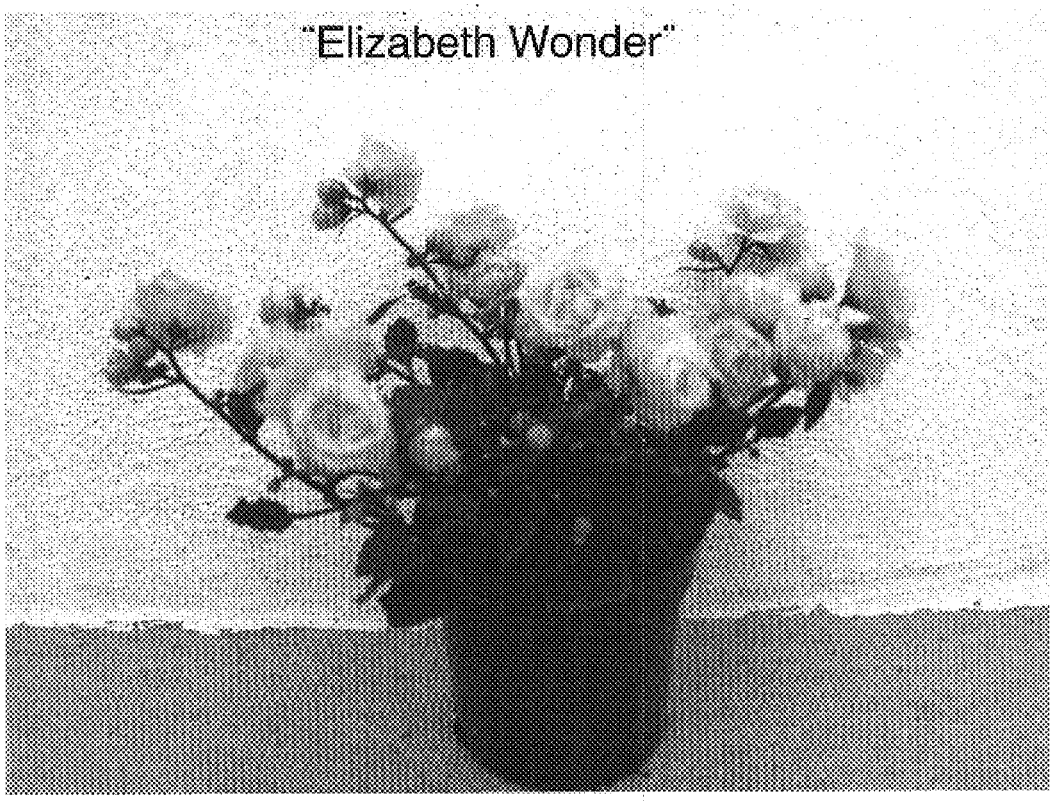
"Elizabeth Wonder"

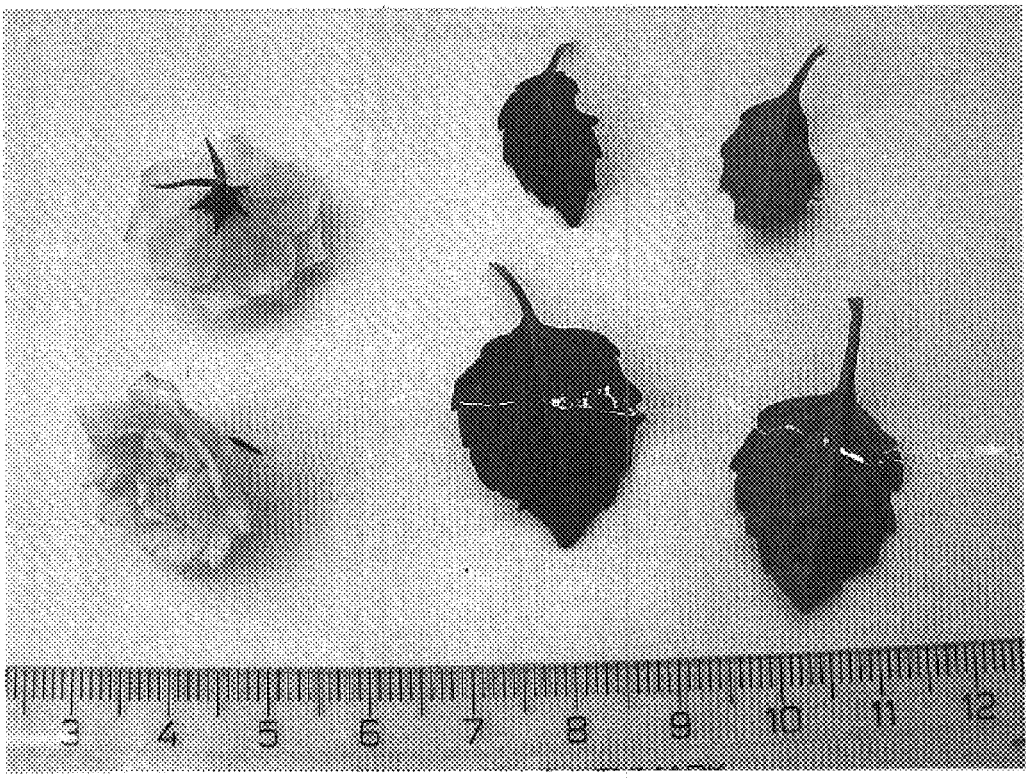
3
4
5
6
7
8
9
10
11
12

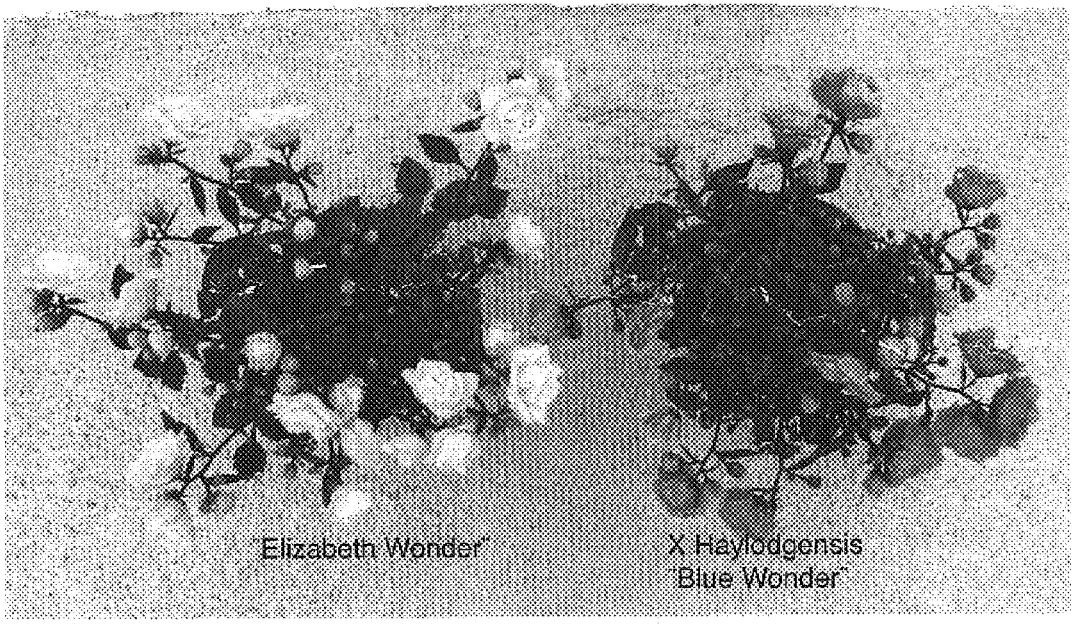
"Elizabeth Wonder"
X Haylodgensis
"Blue Wonder"